United States Patent
Chia et al.

(10) Patent No.: US 6,511,673 B1
(45) Date of Patent: Jan. 28, 2003

(54) MICROBICIDAL COMPOSITION

(75) Inventors: Li Liang Chia, Ambler, PA (US); Megan Anne Diehl, Line Lexington, PA (US); Christine Mary Schultz, Horsham, PA (US); Dolores Ann Shaw, Collegeville, PA (US); Eileen Fleck Warwick, Lansdale, PA (US); Terry Michael Williams, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 54 days.

(21) Appl. No.: 09/833,270

(22) Filed: Apr. 12, 2001

Related U.S. Application Data

(60) Provisional application No. 60/203,306, filed on May 10, 2000.

(51) Int. Cl.$^7$ ............ A61K 7/00; A61K 7/075; A61K 31/425; A01N 25/08; C07D 513/00
(52) U.S. Cl. .......... 424/401; 424/70.28; 424/409; 514/372; 514/373; 548/213
(58) Field of Search .............. 424/401, 70.28, 424/409; 514/372, 373; 548/213

(56) References Cited

U.S. PATENT DOCUMENTS

| | | | | |
|---|---|---|---|---|
| 5,037,989 A | * | 8/1991 | Willingham et al. ........ | 548/213 |
| 5,756,005 A | * | 5/1998 | Ghosh et al. ................ | 252/405 |
| 5,889,034 A | * | 3/1999 | Bolton et al. ................ | 514/373 |
| 5,989,533 A | * | 11/1999 | Deegan et al. ........... | 424/70.28 |
| 6,270,786 B1 | * | 8/2000 | Leeming et al. ............ | 424/409 |
| 6,255,331 B1 | * | 7/2001 | El A'mma et al. ......... | 514/372 |

FOREIGN PATENT DOCUMENTS

| | | |
|---|---|---|
| EP | 0 194 466 A2 * | 2/1986 |
| WO | WO 96/00060 | 1/1996 |

OTHER PUBLICATIONS

Derwent Abstract of EP 0 194 466, Sep. 1986.*

* cited by examiner

*Primary Examiner*—Sreeni Padmanabhan
*Assistant Examiner*—Michael A. Willis
(74) *Attorney, Agent, or Firm*—Thomas J. Howell

(57) ABSTRACT

Microbicidal compositions containing selected ratios of a non-halogenated 2-alkyl-3-isothiazolone and one or more ($C_1$–$C_7$) esters of para-hydroxybenzoic acid are disclosed as improved formulations for controlling microbial growth. In particular the combination of 2-methyl-3-isothiazolone with a mixture of methyl para-hydroxybenzoate and propyl para-hydroxybenzoate is especially effective as a microbicidal component in personal care compositions.

20 Claims, No Drawings

MICROBICIDAL COMPOSITION

CROSS REFERENCE TO RELATED PATENT APPLICATIONS

This is a non-provisional application of prior pending U.S. provisional application serial No. 60/203,306 filed May 10, 2000.

BACKGROUND

This invention relates to the improved efficacy of combinations of selected microbicides in selected concentrations and ratios to provide microbicidal activity at lower concentrations and faster response times than would otherwise be observed for the individual microbicides alone. In particular, this invention relates to the improved efficacy of selected microbicide combinations in personal care formulations.

Microbicides are used commercially to prevent the growth of microbes in a variety of loci, such as cooling towers, metal working fluid systems, paints and cosmetics. One of the more important classes of microbicides is 3-isothiazolones, which have achieved commercial success because they are very effective in preventing microbial growth under a wide variety of conditions and in a variety of loci. Another class of commercial microbicides is paraben esters or parabens, that is, alkyl esters of para-hydroxybenzoic acid; these materials are useful in a variety of applications, specifically against yeast and molds. For example, Patent Application WO 96/00060 discloses the use of parabens as a microbicidal preservative in topical therapeutic and cosmetic compositions containing N-acetyl-L-cysteine.

Sometimes the commercial microbicides, used individually, cannot provide effective control of microorganisms even at high use concentrations due to weak activity against certain types of microorganisms. Without effective microbial control, loss of product, inferior product, production time loss, health hazard, and other problems may occur in the loci treated. Combinations of different microbicidal agents are sometimes used to provide overall control of microorganisms in a particular end use environment, for example, in personal care formulations, such as skin care formulations (sunscreens, lotions and creams). However, many of these microbicide combinations are deficient in their overall performance due to a variety of reasons, for example, incompatibility of the individual active ingredients, high use levels of each component required for effective microbicidal activity or limited control of microorganisms due to the reduced lifetime of one of the active ingredients in the combination. There is a need for control of various of microorganisms that does not rely on high use levels of combinations of different microbicidal agents, but provides effective overall control of the microorganisms that is both quick and long lasting.

The problem addressed by the present invention is to overcome deficiencies of previous microbicide combinations by providing a combination of microbicidal agents that is more effective than the individual microbicides used alone or that can be used at overall lower levels while providing efficacy similar to the original individual microbicide levels.

SUMMARY OF INVENTION

The present invention provides a microbicidal composition comprising (a) a non-halogenated 2-alkyl-3-isothiazolone selected from one or more substituted or unsubstituted 2-($C_1$–$C_4$)alkyl-3-isothiazolones and (b) a ($C_1$–$C_7$) ester of para-hydroxybenzoic acid, wherein the non-halogenated 2-alkyl-3-isothiazolone and the ($C_1$–$C_7$) ester of para-hydroxybenzoic acid are present in a weight/weight ratio of 1:0.2 to 1:500.

In one embodiment the present invention provides a microbicidal composition as described above wherein the non-halogenated 2-alkyl-3-isothiazolone is 2-methyl-3-isothiazolone and the ($C_1$–$C_7$) ester of para-hydroxybenzoic acid is a mixture of methyl para-hydroxybenzoate and propyl para-hydroxybenzoate.

The present invention further provides a method of inhibiting the growth of microorganisms in a personal care composition comprising introducing to the personal care composition a microorganism-inhibiting amount of a microbicidal composition, the microbicidal composition comprising (a) a non-halogenated 2-alkyl-3-isothiazolone selected from one or more substituted or unsubstituted 2-($C_1$–$C_4$) alkyl-3-isothiazolones and (b) a ($C_1$–$C_7$) ester of para-hydroxybenzoic acid, wherein the non-halogenated 2-alkyl-3-isothiazolone and the ($C_1$–$C_7$) ester of para-hydroxybenzoic acid are present in a weight/weight ratio of 1:0.2 to 1:500.

In another aspect the present invention provides a personal care composition comprising (a) an ingredient selected from one or more of UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents, and (b) a microbicidal composition as described above.

DETAILED DESCRIPTION

We have discovered that non-halogenated 2-alkyl-3-isothiazolones may be combined with para-hydroxybenzoic acid esters to provide enhanced microbicidal efficacy at a combined active ingredient level lower than that of the individual 3-isothiazolone or para-hydroxybenzoic acid ester. We have discovered that selected 3-isothiazolones and selected para-hydroxybenzoic acid esters used in specific relative proportions unexpectedly provide the microbicidal compositions of the present invention having enhanced microbicidal efficacy. Preferably the microbicidal compositions are substantially free of halogenated 3-isothiazalone compounds and metal salt stabilizers, such as nitrate or magnesium salts; these "salt-free" microbicidal compositions are especially useful to protect personal care compositions against microbial contamination.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algaecides. The term "microorganism" includes, for example, fungi, yeast, bacteria and algae. The term "locus" refers to an industrial system or product subject to contamination by microorganisms. "Salt-free" means that the composition contains zero or up to 0.5%, preferably zero or up to 0.1%, and more preferably zero or up to 0.01%, of metal salt, based on weight of the composition. Preferably the microbicidal composition is substantially free of halogenated 3-isothiazolone; that is, zero or up to 3%, preferably zero or up to 1% and more preferably zero or up to 0.5%, of halogenated 3-isothiazolone may be present, based on combined weight of halogenated 3-isothiazolone and non-halogenated 2-alkyl-3-isothiazolone.

The following abbreviations are used throughout the specification: cfu=colony forming units, ppm=parts per million by weight (weight/weight), g=gram, mL=milliliter. Unless otherwise specified, ranges listed are to be read as inclusive and combinable, temperatures are in degrees centigrade (° C.), and references to percentages (%) are by weight.

Any non-halogenated 3-isothiazolone (NHITA) compound is useful in the compositions of the present invention. Preferably, the NHITA compound is a water soluble compound, that is, having a water solubility typically greater than about 5%. Suitable NHITA compounds include, for example, substituted and unsubstituted non-halogenated 2-($C_1$–$C_4$)alkyl-3-isothiazolones, where the substituted 3-isothiazolones may contain ($C_1$–$C_4$)alkyl groups at one or both of the 4- and 5- positions of the isothiazolone ring. Specific NHITA compounds include, for example, 2-methyl-3-isothiazolone (MI), 2-ethyl-3-isothiazolone, 2-propyl-3-isothiazolone, 2-isopropyl-3-isothiazolone, 2-butyl-3-isothiazolone (including 2-n-butyl-, 2-isobutyl- and 2-secbutyl- derivatives). Preferably, the NHITA compound is 2-methyl-3-isothiazolone.

Para-hydroxybenzoic acid esters useful in the compositions of the present invention include, for example, the ($C_1$–$C_7$) esters of para-hydroxybenzoic acid, such as methyl, ethyl, propyl (including n-propyl and isopropyl derivatives), butyl (including n-butyl, isobutyl, secbutyl and tertbutyl derivatives), pentyl (including branched and linear variations), hexyl (including branched and linear variations), heptyl and benzyl esters of para-hydroxybenzoic acid. Preferably, the alkyl esters are selected from one or more of methyl para-hydroxybenzoate, ethyl para-hydroxybenzoate, propyl para-hydroxybenzoate, butyl para-hydroxybenzoate and benzyl para-hydroxybenzoate (known as paraben esters); more preferably, the parabens esters are a mixture of the methyl para-hydroxybenzoate and propyl para-hydroxybenzoate.

The ratio of non-halogenated 2-alkyl-3-isothiazolone to ($C_1$–$C_7$) ester of para-hydroxybenzoic acid in the compositions of the present invention is typically from 1:0.2 to 1:500, preferably from 1:0.5 to 1:200, more preferably from 1:0.6 to 1:100 and most preferably from 1:1 to 1:60. The concentration of total active ingredient, comprising the non-halogenated 2-alkyl-3-isothiazolone and ($C_1$–$C_7$) ester of para-hydroxybenzoic acid, in the compositions of the present invention, typically ranges from 1 to 75%, preferably from 2 to 50%, more preferably from 5 to 20% and most preferably from 5 to 10%, for "concentrate" formulations, based on total weight of the formulated composition; and from 50 to 15,000 ppm, preferably from 100 to 10,000 ppm, more preferably from 150 to 6,000 ppm and most preferably from 300 to 5,000 ppm, in the final "end use" formulation, such as a personal care formulation. Typically the concentration of non-halogenated 2-alkyl-3-isothiazolone in final "end use" formulations is from 20 to 250 ppm, preferably from 30 to 150 ppm and more preferably from 50 to 100 ppm.

Optionally, other microbicidal agents may be present in the microbicide compositions of the present invention provided that the physical and chemical stability of the composition is substantially unaffected. For example, limited amounts of halogenated 3-isothiazolones, such as, for example, 5-chloro-2-methyl-3-isothiazolone, may be present. Other suitable microbicidal agents that may be present in the microbicide compositions include, for example, 3-iodo-2-propynylbutylcarbamate, 2-bromo-2-nitropropanediol, benzyl alcohol, phenoxyethanol, glutaric dialdehyde, 2-n-octyl-3-isothiazolone, sodium and zinc salts of 2-pyridinethiol-1-oxide, tris(hydroxymethyl) nitromethane, dimethylol-dimethylhydantoin, monomethylol-dimethylhydantoin and benzisothiazolone. Preferably the composition is substantially free of other microbicidal agents; that is, zero or up to 20%, preferably zero or up to 5%, and more preferably zero or up to 1%, of other microbicidal agents may be present, based on the weight of the composition.

Those skilled in the art will recognize that the NHITA and paraben ester components of the present invention may be added to a locus sequentially, simultaneously, or may be combined before being added to the locus.

When the microbicides are combined prior to being added to a locus, the combination is typically provided in the form of a concentrate solution or dispersion; for example, solutions may be based on water-soluble organic solvents, including for example: polyols (alkyleneoxide glycols such as ethylene glycol, diethylene glycol, polyethylene glycols, propylene glycol, dipropylene glycol and polypropylene glycols; alkanediols such as 1,3-butanediol, 1,2-pentanediol, 1,4-pentanediol and 1,5-pentanediol; and alkanetriols such as glycerol); ($C_1$–$C_4$)alkyl esters of acetic acid and propionic acid (such as methyl acetate, ethyl acetate, ethyl propionate and butyl acetate); ($C_2$–$C_4$) alcohols (such as ethanol, n-propanol, isopropanol, n-butanol, isobutyl alcohol, sec-butyl alcohol and tert-butyl alcohol); benzyl alcohol; and phenoxyethanol. Preferably the water-soluble organic solvent is selected from one or more of propylene glycol, dipropylene glycol, 1,3-butanediol, benzyl alcohol and phenoxyethanol. Alternatively, the concentrates may be provided as aqueous dispersions (together with surfactants), aqueous mixtures of the aforementioned water-soluble organic solvents, or as solid formulations containing suitable carrier materials.

When the microbicides are combined prior to being added to a locus, such combination may optionally contain one or more of solvent, thickeners, anti-freeze agents, colorants, dispersants, surfactants, stabilizers, scale inhibitors and anti-corrosion additives.

The microbicidal compositions of the present invention can be used to inhibit the growth of microorganisms by introducing a microbicidally effective amount of the compositions onto, into, or at a locus subject to microbial attack. Suitable loci include, for example: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions; dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas.

Preferably, the microbicidal compositions of the present invention are used to inhibit the growth of microorganisms at a locus selected from one or more of emulsions, dispersions, paints, latexes, household products, cosmetics, toiletries, shampoos, soaps, detergents and industrial cleaners. In particular, the microbicidal compositions are useful in personal care applications, such as hair care (for example, shampoo and dyes) and skin care (for example, sunscreens, cosmetics, soaps, lotions and creams) formulations.

The personal care compositions of the present invention, besides comprising the microbicidal combination of a non-halogenated 2-alkyl-3-isothiazolone and a ($C_1$–$C_7$) ester of para-hydroxybenzoic acid, also comprise one or more ingredients selected from UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents.

Suitable UV radiation-absorbing agents (including chemical absorbers and physical blockers) include, for example, oxybenzone, dioxybenzone, sulisobenzone, menthyl anthranilate, para-aminobenzoic acid, amyl para-dimethylaminobenzoic acid, octyl para-dimethylaminobenzoate, ethyl 4-bis(hydroxypropyl)para-aminobenzoate, polyethylene glycol (PEG-25) para-aminobenzoate, ethyl 4-bis(hydroxypropyl)aminobenzoate, diethanolamine para-methyoxycinnamate, 2-ethoxyethyl para-methoxycinnamate, ethylhexyl para-methoxycinnamate, octyl para-methoxycinnamate, isoamyl para-methoxycinnamate, 2-ethylhexyl-2-cyano-3,3-diphenylacrylate, 2-ethylhexyl salicylate, homomenthyl salicylate, glyceryl aminobenzoate, triethanolamine salicylate, digalloyl trioleate, lawsone with dihydroxyacetone, 2-phenylbenzimidazole-5-sulfonic acid, 4-methylbenzylidine camphor, avobenzone, titanium dioxide and zinc oxide. Alternatively, UV radiation-absorbing agents such as triazines, benzotriazoles, vinyl group-containing amides, cinnamic acid amides and sulfonated benzimidazoles may also be used.

Suitable surfactants include, for example, nonionic, anionic, cationic and amphoteric surfactants and mixtures thereof; such as PPG 28 Buteth 35, PEG 75 lanolin, perfluoropolymethyl isopropyl ether, octoxynol-9, PEG-25 hydrogenated castor oil, polyethylene terephthalate, polyethylene glycol 25 glyceryl trioleate, oleth-3 phosphate, PPG-5-ceteth-10 phosphate, PEG-20 methyl glucose ether, glycereth-7-triacetate and N-alkyl substituted lactam (such as N-octyl pyrrolidone).

Suitable thickeners or rheology modifiers include, for example, hydrophobically modified nonionic ethoxylated urethanes, polycarboxylic acid thickeners such as acrylates/steareth-20 methacrylate copolymer, carbomers, acrylates copolymer and acrylates $C_{10–30}$ alkyl acrylate crosspolymer.

The personal care compositions improved by the method of this invention include, for example:
 (a) hair care formulations, including shampoos, hair dyes, hair conditioners, gels, mousses and hair sprays; and
 (b) skin care and nail care formulations, including nail coatings, cosmetics, astringents, depilatories, facial make-up formulations, sunscreens and sunblocks, pre-moistened wipes, hand creams, hand and body soaps, and hand and body lotions.

The cosmetic formulations typically contain water, film forming materials, emulsifiers, softeners, emollients, oils, stabilizers, thickeners, neutralizers, perfume, colorants, pigments and combinations thereof. The sunscreen formulations typically contain UV radiation-absorbing agents, water, film forming materials, emulsifiers, emollients, waterproofing agents, oils, stabilizers, thickeners, preservatives, perfume, colorants, insecticides, humectants and combinations thereof.

Optionally, other additives, such as additional film forming agents, plasticizers, antifoaming agents, leveling aids, excipients, vitamins, natural extracts, proteins, sequestrants, dispersants, antioxidants, suspending agents and solvents may be added to the personal care formulations described above. Suitable solvents include, for example, $C_1$–$C_{12}$ straight or branched chain alcohols such as ethanol, isopropanol, or propanol; alkyl esters such as ethyl acetate; ketones; and combinations thereof.

Some embodiments of the invention are described in detail in the following Examples. All ratios, parts and percentages are expressed by weight unless otherwise specified, and all reagents used are of good commercial quality unless otherwise specified. Abbreviations used in the Examples and Tables are listed below with the corresponding descriptions:

MI=2-methyl-3-isothiazolone
MP=methyl para-hydroxybenzoate
PP=propyl para-hydroxybenzoate
DU=diazolidinyl urea
IU=imidazolidinyl urea
CFU=colony forming units
SI=synergy index

EXAMPLE 1

One aspect of the present invention is demonstrated by the synergistic combination of 2-methyl-3-isothiazolone (MI) with (a) propyl para-hydroxy-benzoate (PP) or with (b) a mixture of methyl para-hydroxybenzoate (MP) and propyl para-hydroxybenzoate (PP), referred to as [MP+PP].

Synergism was determined by an industrially accepted method described by Kull, F. C.; Eisman, P. C.; Sylwestrowicz, H. D. and Mayer, R. L., in *Applied Microbiology* 9:538–541 (1961), using the ratio determined by the formula:

$$Q_a/Q_A + Q_b/Q_B = \text{Synergy Index ("SI")}$$

wherein:
 $Q_A$=concentration of compound A in ppm, acting alone, which produced an end point (MIC of Compound A).
 $Q_a$=concentration of compound A in ppm, in the mixture, which produced an end point.
 $Q_B$=concentration of compound B in ppm, acting alone, which produced an end point (MIC of Compound B).
 $Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture. The minimum inhibitory concentration (MIC) of a microbicide is the lowest concentration tested under a specific set of conditions that prevents the growth of added microorganisms.

Test Medium Condition 1 (Two-Fold Serial Dilution)
Synergism of combinations of microbicides was determined using standard MIC assays in trypticase soy broth medium ("TSB" medium). In this method, a range of concentrations was tested by preparing two-fold serial dilutions of the compound tested in 96-well microtiter plates. All liquid media transfers were performed with calibrated single or multichannel digital pipettors. Stock solutions of the microbicides were prepared in appropriate solvents and added to the TSB medium. All subsequent dilutions in plates were made using an automated liquid handling system. Final concentrations of microbicides were obtained by making two-fold serial dilutions in two directions in the microtiter plate. Each plate contained a control row for each individual microbicide, hence, the MIC values for each microbicide were determined simultaneously. A cell suspension of either *Aspergillus niger* (*A. niger*, ATCC #16404) or *Candida albicans* (*C. albicans*, ATCC #10231), adjusted to provide $1 \times 10^5$ cells per mL in each well, was added to the microtiter plates. The plates were visually evaluated for microbial growth (turbidity) to determine the MIC after incubation at 25° C. for one week.

The test results for demonstration of synergy of the microbicide combinations of the present invention are shown below in Table 1. In each test, Compound A was MI and Compound B was another commercial microbicide. The table shows the specific combination of Compound A and Compound B, the end-point activity in ppm measured by the MIC for Compound A alone ($Q_A$), for Compound B alone ($Q_B$), for Compound A in the mixture ($Q_a$), or for Compound B in the mixture ($Q_b$), the calculated SI value, and the range of synergistic ratios for each combination tested (Compound A:Compound B).

TABLE 1

| Microorganism | $Q_A$ | $Q_a$ | $Q_B$ | $Q_b$ | SI | A:B |
|---|---|---|---|---|---|---|
| A. niger | 250 | 125 | 594 | 74 | 0.62 | 1:0.6 |
| | 250 | 125 | 594 | 148 | 0.75 | 1:1.2 |
| | 250 | 63 | 594 | 297 | 0.75 | 1:4.7 |
| | 250 | 31 | 594 | 297 | 0.62 | 1:9.6 |

Compound A = 2-methyl-3-isothiazolone (MI)
Compound B = propyl para-hydroxybenzoate (PP)

The synergistic ratios of MI:PP in this medium range from 1:0.6 to 1:9.6.

Test Medium Condition 2 (Ten-Fold Serial Dilution)

In a manner similar to that described above for Test Medium Condition 1, the synergism of combinations of microbicides determined in TSB by conducting high resolution MIC assays in the presence of various concentrations of MI. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient. The plates were visually evaluated for microbial growth (turbidity) to determine the MIC after incubation at 25° C. for 72 hours.

The test results for demonstration of synergy of the microbicide combinations of the present invention are shown below in Tables 2 and 3.

TABLE 2

| Microorganism | $Q_A$ | $Q_a$ | $Q_B$ | $Q_b$ | SI | A:B |
|---|---|---|---|---|---|---|
| A. niger | 150 | 100 | 200 | 60 | 0.97 | 1:0.6 |
| | 150 | 75 | 200 | 80 | 0.90 | 1:1.1 |
| C. albicans | 100 | 75 | 300 | 60 | 0.95 | 1:0.8 |

Compound A = 2-methyl-3-isothiazolone (MI)
Compound B = propyl para-hydroxybenzoate (PP)

The synergistic rations of MI-PP in this medium range from 1:0.6 to 1:1.1.

TABLE 3

| Microorganism | $Q_A$ | $Q_a$ | $Q_B$ | $Q_b$ | SI | A:B |
|---|---|---|---|---|---|---|
| A. niger | 150 | 100 | 300 | 60 | 0.87 | 1:0.6 |
| | 150 | 100 | 300 | 80 | 0.93 | 1:0.8 |
| | 150 | 75 | 300 | 100 | 0.83 | 1:1.0 |
| C. albicans | 100 | 75 | 400 | 60 | 0.90 | 1:0.8 |
| | 100 | 75 | 400 | 80 | 0.95 | 1:1.1 |

Compound A = 2-methyl-3-isothiazolone (MI)
Compound B = methyl para-hydroxybenzoate/propyl para-hydroxybenzoate (2:1 weight ratio MP/PP)

The synergistic ratios of MI/[MP+PP] in this medium range from 1:0.6 to 1:1.1.

EXAMPLE 2

Another aspect of the present invention is demonstrated by the improved performance of a MP/PP mixture (2:1 weight ratio) or MP when it was combined with a selected amount of MI for use in a body lotion formulation. That is, the microbicidal performance of the MP/PP or MP compositions was significantly enhanced when combined with MI versus use of the paraben esters alone or when the paraben esters were used in combination with other microbicides, such as IU, a typical formaldehyde releasing microbicide.

Anionic Body Lotion Formulation

| INCI* Name | Wt % |
|---|---|
| Water | 74.65 |
| Glycerin (humectant) | 5.00 |
| Disodium Ethylenediaminetetraacetic Acid (sequestrant) | 0.05 |
| Magnesium Aluminum Silicate (rheology modifier) | 1.00 |
| Carbomer (thickener/stabilizer) | 7.50 |
| Stearic Acid (emulsifier) | 2.00 |
| Cetyl Alcohol (emollient) | 0.25 |
| Glycol Stearate and Other Ingredients (emulsifier) | 1.50 |
| Glycerol Stearate (emulsifier) | 1.00 |
| Glycine Soja (Soybean) Sterol (emulsifier) | 0.25 |
| Tocopherol Acetate (vitamin) | 0.10 |
| Cetearyl alcohol & dicetyl phosphate & ceteth-10 phosphate (emulsifier) | 0.50 |
| Lecithin (emulsifier) | 0.10 |
| Retinyl Palmitate (vitamin) | 0.10 |
| Helianthus Annuus (Sunflower) Seed Oil (emollient) | 3.00 |
| $C_{11-13}$ Isoparaffin (solvent) | 1.00 |
| Dimethicone (excipient) | 0.50 |
| Triethanolamine (neutralizing agent) | 0.80 |

*International Nomenclature of Chemical Ingredients

Microbicide Efficacy

The microbicidal efficacy of 2-methyl-3-isothiazolone microbicide in combination with paraben ester microbicides was determined in an anionic body lotion using a modified USP microbiological test method: aliquots of the anionic body lotion were prepared and dosed with the following microbicide packages:

(a) 50 ppm 2-methyl-3-isothiazolone/[2000 ppm methyl para-hydroxybenzoate+1000 ppm propyl para-hydroxybenzoate]

(b) comparative: 2500 ppm imidazolidinyl urea/[2000 ppm methyl para-hydroxybenzoate+1000 ppm propyl para-hydroxybenzoate]

All levels tested were based on manufacturer's recommended use levels. The body lotion samples were inoculated with $10^5$–$10^6$ cfu (colony forming units)/mL of a mixed fungal and bacterial inoculum which included *Candida albicans* (ATCC No. 10231), *Aspergillus niger* (ATCC No.

16404), *Escherichia coli* (ATCC No. 8739), *Pseudomonas aeruginosa* (ATCC No. 9027) and *Staphylococcus aureus* (ATCC No. 6538).

The samples were inoculated at time zero, stored at 25° C. and monitored for the survival of microorganisms at 3, 7, 14 and 28 days using a standard streak plate method.

A growth rating system was assigned as follows, from complete microbial control ("0" rating) to no microbial control ("4" rating):

| Growth Rating | Colony Forming Units (cfu)/g |
|---|---|
| 0 | <10 |
| 1 | $10^2-10^3$ |
| 2 | $10^3-10^4$ |
| 3 | $10^4-10^5$ |
| 4 | $>10^5$ |

The results of the bacterial and fungal challenge test evaluations of microbicide combinations in an anionic body lotion are shown in Tables 4 and 5. The 50 ppm 2-methyl-3-isothiazolone/[2000 ppm methyl para-hydroxybenzoate+ 1000 ppm propyl para-hydroxybenzoate], referred to as MI/[MP+PP], was compared to a commercial microbicide package of IU/[MP+PP]. The untreated formulation (4-0) supported high levels of viable bacteria over the 28 day test period (Table 4). The MI/[MP+PP] combination (4-4) resulted in a reduction in bacteria to below to detectable limits (<10 cfu/g or growth rating of 0) within three days and no viable bacteria were recovered over the duration of the test. The other paraben ester microbicide package (4-1, comparative) based on 2500 ppm IU/[2000 ppm MP+1000 ppm PP] required more than 3 days contact to reduce the bacteria to the same level as the MI/[MP+PP] combination (4-4). This demonstrates the enhanced "knock-down" or speed-of-kill properties of the MI/[MP+PP] combination relative to the commercial microbicide package. The relative ineffectiveness of the individual microbicides in this test medium is represented by 4-2 and 4-3 in Table 4.

The anionic body lotion was also susceptible to fungal contamination. A high level of fungi was detected in the untreated lotion (5-0) throughout the test (Table 5). Similar to the bacterial evaluation, the MI/[MP+PP] formulation (5-4) reduced the fungal contamination to <10 cfu/g within three days. The other paraben ester microbicide package (5-2, comparative) based on IU/[MP+PP] demonstrated only a slight to moderate reduction in fungal contamination over the duration of the test. The relative ineffectiveness of the individual microbicides in this test medium is represented by 5-1 and 5-3 in Table 5.

TABLE 4

Antibacterial Efficacy in Anionic Body Lotion

| | | Active Ingredient | Growth Rating vs Time | | | |
|---|---|---|---|---|---|---|
| ID | Combination | (ppm) | 3 days | 7 days | 14 days | 28 days |
| 4-0 | Control | 0 | 4 | 4 | 4 | 4 |
| 4-1 | IU/[MP + PP] | 2500/[2000 + 1000] | 4 | 0 | 0 | 0 |
| 4-2 | MP + PP | 2000 + 1000 | * | * | * | * |
| 4-3 | MI | 50 | 4 | 4 | 3 | 4 |
| 4-4 | MI/[MP + PP] | 50/[2000 + 1000] | 0 | 0 | 0 | 0 |

*expected to be ineffective based on known weak performance towards bacteria

TABLE 5

Antifungal Efficacy in Anionic Body Lotion

| | | Active Ingredient | Growth Rating vs Time | | | |
|---|---|---|---|---|---|---|
| ID | Combination | (ppm) | 3 days | 7 days | 14 days | 28 days |
| 5-0 | Control | 0 | 4 | 4 | 4 | 4 |
| 5-1 | IU | 2500 | * | * | * | * |
| 5-2 | IU/[MP + PP] | 2500/[2000 + 1000] | 4 | 3 | 3 | 2 |
| 5-3 | MI | 50 | 2 | — | 3 | 3 |
| 5-4 | MI/[MP + PP] | 50/[2000 + 1000] | 0 | 0 | 1 | 0 |

*expected to be ineffective based on known weak performance towards fungi

The combination of MI with paraben esters offers significantly enhanced microbicidal activity relative to a commercial microbicidal package, such as IU/[MP+PP]; that is, less contact time is required for microbial control and more effective overall control of fungi is observed, compared to current preservative packages. Thus, the MI/paraben ester combinations offer an effective alternative to commerical microbicidal formulations containing formaldehyde donors.

EXAMPLE 3

Another aspect of the present invention is demonstrated by the improved performance of a [MP+PP] mixture (2:1 weight ratio) or MP when it is combined with a selected amount of MI for use in a sunscreen or sunblock formulation. That is, the microbicidal performance of the [MP+PP] or MP compositions is significantly enhanced when combined with MI versus use of the paraben esters alone or when the paraben esters were used in combination with other microbicides, such as IU or DU, typical formaldehyde releasing microbicides.

Sunscreen I (Chemical Absorber)

A sunscreen based on an oil in water formulation using a chemical absorber is representative of that used in Europe. The sun protection factor (SPF) is approximately 12–15, final pH is 6.8. Composition of the sunscreen evaluated is presented below:

| INCI* Name | Wt % |
|---|---|
| Water | 65.3 |
| Carbomer (thickener/stabilizer) | 10 |
| Propylene Glycol (humectant) | 2.0 |
| Ethylhexyl Palmitate (emollient) | 8 |
| Octocrylene (UVB absorber) | 4 |
| 4-Methylbenzylidene Camphor (UVB absorber) | 4 |
| Stearic Acid (emulsifier) | 2 |
| Butyl Methoxydibenzoylmethane (UVA absorber) | 2 |
| Ethylene Glycol Distearate (opacifier) | 1 |
| Cetyl Alcohol (emollient) | 0.5 |
| PEG-40 Stearate (emulsifier) | 0.2 |
| Sodium Hydroxide (neutralizing agent) | 1 |

*International Nomenclature of Chemical Ingredients

Microbicide Efficacy

The microbicidal efficacy study was conducted using a modification of a CTFA (Cosmetics, Toiletries and Fragrances Association) method. Samples of sunscreen were treated with MI microbicide alone and in combination with MP and PP. An untreated control (6-0 and 7-0 in Tables 6 and 7, respectively) was included in the test to determine the intrinsic susceptibility of the formulation to microbial contamination.

Sunscreen samples were dosed with the microbicide(s). The samples were inoculated with a mixed pool of common spoilage bacteria or fungi immediately after dosing to obtain approximately $10^6$ colony forming units per gram (cfu/g) of sample for the bacteria and $10^5$ cfu/g of sample for the fungi. Bacterial samples were incubated at 30° C. and fungal samples at 25° C. for the test duration. The organisms in the mixed bacteria and fungal pools were as follows:

| Organism Identification | ATCC number |
|---|---|
| Mixed Bacterial Pool: | |
| Burkholderia cepacia | 17765 |
| Escherichia coli | 8739 |
| Klebsiella pneumoniae | 4352 |
| Pseudomonas aeruginosa | 15442 |
| Staphylococcus aureus | 6538 |
| Mixed Fungal Pool: | |
| Aspergillus niger | 6275 |
| Candida albicans | 11651 |
| Penicillium pinophilum (luteum) | 9644 |

The samples were monitored for survival of microorganisms at 1, 2, 3 and 4 weeks. Samples were deactivated by making 3 subsequent 1:10 dilutions in Letheen Broth. Viable counts were determined by spreading 0.1 mL of each dilution onto Letheen Agar plates. Plates were read after an incubation period of 48 hours at 30° C. for bacteria and one week at 25° C. for fungi. Microbicidal systems were considered effective if there was no more than a trace of contamination at one week and no detectable organisms at two, three and four weeks.

Table 6 summaries the antifungal study. The MI/[MP+PP] combinations (6-2, 6-4 and 6-6) provided significant reductions in fungi concentrations relative to the fungal control observed for the individual microbicides (6-1, 6-3, 6-5 and 6-8). The other paraben ester microbicide package (6-9, comparative) based on 2400 ppm IU/[2000 ppm MP+1000 ppm PP] provided little or no control to reduce the fungi concentration relative to the untreated control (6-0). This demonstrates the enhanced "knock-down" and overall control properties of the MI/[MP+PP] combination relative to the commercial microbicide package (6-9).

Table 7 summaries the antibacterial study. The MI/[MP+PP] combinations (7-2, 7-4, and 7-6) provided significant reductions in bacterial growth relative to the bacterial control observed for the individual microbicides (7-1, 7-3, 7-5 and 7-7). This demonstrates the enhanced "knock-down" effectiveness and overall duration of control demonstrated by the MI/[MP+PP] combination relative to the individual microbicides used alone.

TABLE 6

Antifungal Efficacy in Sunscreen I

| ID Combination | Active Ingredient (ppm) | Growth (cfu/g) vs Time | | | |
|---|---|---|---|---|---|
| | | 1 week | 2 weeks | 3 weeks | 4 weeks |
| 6-0 Control | 0 | $10^5$ | $10^5$ | $10^5$ | $10^5$ |
| 6-1 MI | 50 | $10^4$ | $10^4$ | $10^5$ | $10^6$ |
| 6-2 MI/[MP + PP] | 50/[2000 + 1000] | $10^3$ | 0 | $10^2$ | 10 |
| 6-3 MI | 75 | $10^5$ | $10^4$ | $10^4$ | $10^5$ |
| 6-4 MI/[MP + PP] | 75/[2000 + 1000] | $10^2$ | 0 | 0 | 0 |
| 6-5 MI | 100 | $10^5$ | $10^5$ | $10^5$ | $10^5$ |

TABLE 6-continued

Antifungal Efficacy in Sunscreen I

| ID Combination | Active Ingredient (ppm) | Growth (cfu/g) vs Time | | | |
|---|---|---|---|---|---|
| | | 1 week | 2 weeks | 3 weeks | 4 weeks |
| 6-6 MI/[MP + PP] | 100/[2000 + 1000] | 0 | 0 | 0 | 0 |
| 6-7 IU | 2400 | ** | ** | ** | ** |
| 6-8 MP + PP | 2000 + 1000 | $10^4$ | $10^5$ | $10^5$ | $10^5$ |
| 6-9 IU/[MP + PP] | 2400/[2000 + 1000] | $10^4$ | $10^4$ | $10^5$ | $10^6$ |

**expected to be ineffective based on known weak performance towards fungi

TABLE 7

Antibacterial Efficacy in Sunscreen I

| ID Combination | Active Ingredient (ppm) | Growth (cfu/g) vs Time (weeks) | | | |
|---|---|---|---|---|---|
| | | 1 week | 2 weeks | 3 weeks | 4 weeks |
| 7-0 Control | 0 | $10^8$ | $10^8$ | $10^7$ | $10^7$ |
| 7-1 MI | 50 | $10^4$ | $10^3$ | $10^4$ | 0 |
| 7-2 MI/[MP + PP] | 50/[2000 + 1000] | $10^4$ | $10^4$ | 0 | 0 |
| 7-3 MI | 75 | $10^3$ | 0 | $10^3$ | 0 |
| 7-4 MI/[MP + PP] | 75/[2000 + 1000] | $10^3$ | 0 | 0 | 0 |
| 7-5 MI | 100 | $10^2$ | 0 | 0 | 0 |
| 7-6 MI/[MP + PP] | 100/[2000 + 1000] | 0 | 0 | 0 | 0 |
| 7-7 MP + PP | 2000 + 1000 | $10^7$ | $10^5$ | $10^7$ | $10^7$ |

Sunscreen II (Inorganic Blocker)

Another type of sunscreen is based on a water-in-oil emulsion containing zinc oxide and titanium dioxide to block ultraviolet light with a sun protection factor (SPF) of approximately 25, final pH is 6.4. Composition of the sunscreen evaluated is presented below:

| INCI* Name | Wt % |
|---|---|
| Cetyldimethicone Copolyol (excipient) | 2.5 |
| Cetyldimethicone (excipient) | 1 |
| Ethylhexyl Stearate (emollient/excipient) | 2.85 |
| Ethylhexyl Palmitate (emollient/excipient) | 121 |
| Mineral Oil (oil phase) | 15 |
| Hydrogenated Polydecene (excipient) | 0.5 |
| Beeswax (film former) | 1 |
| Stearic Acid (emulsifier) | 1 |
| Zinc Oxide (UVA/UVB active) | 12.2 |
| Titanium Dioxide (UVB active) | 1 |
| Sodium Chloride (stabilizer) | 0.5 |
| Water | 50.3 |

*International Nomenclature of Chemical Ingredients

Microbicide Efficacy

The microbicide efficacy study was done using a modification of a USP method. Samples of sunscreen were treated with MI microbicide alone (50% 2-methyl-3-isothiazolone in propylene glycol) and in combination with a [MP+PP] mixture. An untreated control (8-0 in Table 8) was included in the test to determine the intrinsic susceptibility of the formulation to microbial contamination.

A portion of sunscreen was dosed with microbicide(s). The samples were inoculated with a mixed pool of common spoilage fungi immediately after dosing to obtain approximately $10^5$ cfu/g of sample for the fungi. Fungal samples were incubated at 25° C. for the test duration. The organisms in the mixed fungal pool were as follows:

Mixed Fungal Pool

| Organism Identification | ATCC number |
|---|---|
| *Aspergillus niger* | 16404 |
| *Candida albicans* | 10231 |

The samples were monitored for survival of microorganisms at one, two, and four weeks. Samples were deactivated by making a 1:10 dilution in Letheen Broth. One mL of this dilution was plated using Letheen Agar and a pour plate technique to give a limit of detection of 10 cfu/g of sample. Counts of the heavily contaminated samples such as the untreated controls were also done using a most probable number analysis (MPN). Plates were read after an incubation period of one week at 25° C. Microbicidal systems were considered effective if there was no more than a trace of contamination at one week and no detectable organisms at two and four weeks.

Table 8 summaries the antifungal study in this sunscreen medium. The MI/[MP+PP] and MI/MP combinations (8-2, 8-3 and 8-5) provided significant reductions in fungi concentrations relative to the fungal control observed for the individual microbicide MI alone (8-1 and 8-4). The other paraben ester microbicide package (8-6, comparative) based on 3000 ppm DU/[1100 ppm MP+300 ppm PP] provided no reduction in the fungi concentration relative to the untreated control (8-0). This demonstrates the enhanced "knockdown" and overall control properties of the MI/[MP+PP] or MI/MP combinations relative to the commercial microbicide package (8-6).

TABLE 8

Antifungal Efficacy in Sunscreen II

| | | Growth (cfu/g) vs Time | | |
|---|---|---|---|---|
| ID | Combination | Active Ingredient (ppm) | 1 week | 2 weeks | 4 weeks |
| 8-0 | Control | 0 | $10^5$ | $10^5$ | $10^5$ |
| 8-1 | MI | 50 | $10^5$ | $10^5$ | $10^3$ |
| 8-2 | MI/[MP + PP] | 50/[2000 + 1000] | $10^2$ | 0 | 0 |
| 8-3 | MI/MP | 75/1500 | $10^2$ | $10^2$ | 0 |
| 8-4 | MI | 100 | $10^3$ | $10^3$ | $10^2$ |
| 8-5 | MI/[MP + PP] | 100/[2000 + 1000] | 0 | 0 | 0 |
| 8-6 | DU/[MP + PP] | 3000/[1100 + 300] | $10^5$ | $10^5$ | $10^5$ |

We claim:

1. A microbicidal composition comprising:
   (a) a non-halogenated 2-alkyl-3-isothiazolone selected from one or more substituted or unsubstituted 2-($C_1$–$C_4$)alkyl-3-isothiazolones, and
   (b) a ($C_1$–$C_7$) ester of para-hydroxybenzoic acid;
   wherein the non-halogenated 2-alkyl-3-isothiazolone and the ($C_1$–$C_7$) ester of para-hydroxybenzoic acid are present in a weight/weight ratio of 1:0.5 to 1:200 and the microbicidal composition is substantially free of halogenated 3-isothiazolone.

2. The composition of claim 1 wherein the ($C_1$–$C_7$) ester of para-hydroxybenzoic acid is selected from one or more of methyl para-hydroxybenzoate, ethyl para-hydroxybenzoate, propyl para-hydroxybenzoate, butyl para-hydroxybenzoate and benzyl para-hydroxybenzoate.

3. The composition of claim 2 wherein the ($C_1$–$C_7$) ester of para-hydroxybenzoic acid is a mixture of methyl para-hydroxybenzoate and propyl para-hydroxybenzoate.

4. The composition of claim 1 wherein the non-halogenated 2-methyl-3-isothiazolone is selected from one or more of 2-methyl-3-isothiazolone, 2-ethyl-3-isothiazolone, 2-propyl-3-isothiazolone, 2-isopropyl-3-isothiazolone and 2-butyl-3-isothiazolone.

5. The composition of claim 1 wherein the non-halogenated 2-methyl-3-isothiazolone is 2-methyl-3-isothiazolone and the ($C_1$–$C_7$) ester of para-hydroxybenzoic acid is a mixture of methyl para-hydroxybenzoate and propyl para-hydroxybenzoate.

6. The composition of claim 5 wherein the 2-methyl-3-isothiazolone and the mixture of methyl para-hydroxybenzoate and propyl para-hydroxybenzoate are present in a weight ratio of 1:0.6 to 1:100.

7. The composition of claim 1 further comprising a water-soluble organic solvent selected from one or more of ethylene glycol, diethylene glycol, polyethylene glycols, propylene glycol, dipropylene glycol, polypropylene glycols, 1,3-butanediol, 1,2-pentanediol, 1,4-pentanediol, 1,5-pentanediol, glycerol, methyl acetate, ethyl acetate, ethyl propionate, butyl acetate, ethanol, n-propanol, isopropanol, n-butanol, isobutyl alcohol, sec-butyl alcohol, tert-butyl alcohol, benzyl alcohol and phenoxyethanol.

8. The composition of claim 7 wherein the water-soluble organic solvent is selected-from one or more of propylene glycol, dipropylene glycol, 1,3-butanediol, benzyl alcohol and phenoxyethanol.

9. The composition of claim 7 wherein the combined concentration of non-halogenated 2-alkyl-3-isothiazolone and ($C_1$–$C_7$) ester of para-hydroxybenzoic acid is from 5 to 20 weight percent, based on total weight of the composition.

10. A personal care composition comprising:
    (a) an ingredient selected from one or more of UV radiation-absorbing agents, surfactants, rheology modifiers or thickeners, fragrances, moisturizers, humectants, emollients, conditioning agents, emulsifiers, antistatic aids, pigments, dyes, tints, colorants, antioxidants, reducing agents and oxidizing agents;
    (b) a non-halogenated 2-alkyl-3-isothiazolone selected from one or more substituted or unsubstituted 2-($C_1$–$C_4$)alkyl-3-isothiazolones; and
    (c) a ($C_1$–$C_7$) ester of para-hydroxybenzoic acid;
    wherein the non-halogenated 2-alkyl-3-isothiazolone and the ($C_1$–$C_7$) ester of para-hydroxybenzoic acid are present in a weight/weight ratio of 1:0.5 to 1:200 and the composition is substantially free of halogenated 3-isothiazolone.

11. The personal care composition of claim 10 wherein the composition is a hair care formulation.

12. The personal care composition of claim 11 wherein the hair care formulation is selected from one or more of shampoos, hair dyes, hair conditioners, gels, mousses and hair sprays.

13. The personal care composition of claim 10 wherein the composition is a skin care formulation.

14. The personal care composition of claim 13 wherein the skin care formulation is selected from one or more of sunscreens, hand creams, hand lotions and body lotions.

15. A method of controlling or inhibiting the growth of microorganisms in a locus comprising introducing to the locus the composition of claim 1.

16. The method of claim 15 wherein the locus is selected from one or more of emulsions, dispersions, paints, latexes, household products, cosmetics, toiletries, shampoos, soaps, detergents, industrial cleaners.

17. A method of inhibiting the growth of microorganisms in a personal care composition comprising introducing to the personal care composition a microorganism-inhibiting amount of a microbicidal composition, the microbicidal composition comprising:
 (a) a non-halogenated 2-alkyl-3-isothiazolone selected from one or more substituted or unsubstituted 2-($C_1$–$C_4$)alkyl-3-isothiazolones, and
 (b) a ($C_1$–$C_7$) ester of para-hydroxybenzoic acid;
wherein the non-halogenated 2-alkyl-3-isothiazolone and the ($C_1$–$C_7$) ester of para-hydroxybenzoic acid are present in a weight/weight ratio of 1:0.5 to 1:200 and the microbicidal composition is substantially free of halogenated 3-isothiazolone.

18. The method of claim 17 comprising from 50 to 15,000 parts per million, based on total weight of the personal care composition, of the microbicidal composition.

19. The method of claim 17 wherein the ratio of non-halogenated 2-alkyl-3-isothiazolone to ($C_1$–$C_7$) ester of para-hydroxybenzoic acid is from 1:0.6 to 1:100.

20. The composition of claim 1 comprising from zero up to 0.5% of the halogenated 3-isothiazolone, based on combined weight of halogenated 3-isothiazolone and non-halogenated 2-alkyl-3-isothiazolone.

* * * * *